United States Patent
Barco Villalba et al.

(10) Patent No.: US 7,404,327 B2
(45) Date of Patent: Jul. 29, 2008

(54) DIFFUSION NOZZLE FOR AN ULTRASONIC PROBE

(75) Inventors: Armando Barco Villalba, Getafe Madrid (ES); Eduardo Borreguero Galvez, Getafe Madrid (ES); Jose Carlos Ordoñez Carbonero, San Martin de la Vega Madrid (ES); Juan Eusebio Fuentes Carrasquilla, Getafe Madrid (ES); Alfredo Plaza Carrasco, Parla Madrid (ES); Francisco Marquez Marinas, Madrid (ES); Miguel Angel Lopez Lopez, Madrid (ES); Francisco Javier Martinez Castaño, Moraleja de Enmedio Madrid (ES); Jose Luis Esteban Casado, Madrid (ES)

(73) Assignee: Airbus Espana, S.L., Madrid (ES)

( * ) Notice: Subject to any disclaimer, the term of this patent is extended or adjusted under 35 U.S.C. 154(b) by 530 days.

(21) Appl. No.: 11/119,424

(22) Filed: Apr. 29, 2005

(65) Prior Publication Data
US 2005/0279157 A1 Dec. 22, 2005

(30) Foreign Application Priority Data
Dec. 1, 2003 (EP) .................... 03380279

(51) Int. Cl.
*G01N 29/28* (2006.01)
(52) U.S. Cl. ........................................................ 73/644
(58) Field of Classification Search ................ 73/632, 73/644
See application file for complete search history.

(56) References Cited

U.S. PATENT DOCUMENTS 3,420,097 A * 1/1969 Battermann et al. ............ 73/644
4,507,969 A * 4/1985 Djordjevic et al. ............. 73/644
5,373,743 A * 12/1994 Abrahams .................... 73/644

* cited by examiner

*Primary Examiner*—John E Chapman
(74) *Attorney, Agent, or Firm*—Ladas & Parry LLP

(57) ABSTRACT

A suitable diffusion nozzle (20) for an ultrasounds probe using water as coupling agent between a piece under inspection and an acoustic transducer (13) such that the water is driven towards the surface of the material through a propulsion channel (21) surrounded by a plurality of diffusion channels (23) through which air is injected under pressure, forming an insulating screen capable of repelling the drops of water generated on the jet of water striking the surface of the material.

10 Claims, 2 Drawing Sheets

DIFFUSION NOZZLE FOR AN ULTRASONIC PROBE

OBJECT OF THE INVENTION

The present invention refers, in general, to the field of inspection of materials by means of an ultrasounds probe, where jets of water are used as coupling agent.

More specifically, the present invention refers to a suitable nozzle for inspection of a material by means of emitter-receptors of ultrasounds by spurting jets of water, opposite one another and insulated by air barriers, on the two surfaces of said material.

STATE OF THE ART

The use of ultrasound probes is already known, for the inspection of materials in order to detect defects therein. A nozzle for coupling ultrasound to a jet of water is indicated in U.S. Pat. No. 4,558,598.

There the nozzle has a lineal distribution of ultrasonic transducers i.e., an emitter nozzle is postioned at one side of the surface of the material under inspection and, on the other side of the surface to be inspected, a receptor nozzle is placed.

The emitter nozzle receives water which is placed in contact with an ultrasound transduct, spurting a jet of water coupled with acoustic energy towards one of the surfaces of the material. On the other side the receptor nozzle captures the ultrasound energy emitted through the other jet of water which the receptor nozzle emits. Consequently, to achieve continuity of the beam of ultrasounds from the nozzle, which includes the emitter transduct, until its arrival at the receptor transduct, located in the receptor nozzle, both nozzles have to be aligned and opposite one another.

Every loss of signal (attenuation) which is produced between the surfaces of the material under inspection will be due to the heterogeneities said material possesses in its interior.

When a jet of water strikes the surface of the material under inspection, a plurality of drops of water is generated which spurt in all directions.

One drawback of this nozzle derives from the possible perturbation caused by some drop, generated on the jet of water striking the surface, on the jet of water itself and, therefore, the energy transmitted by the jet of water is altered.

As a result, the ultrasound energy received by the receptor transduct is disfigured i.e., the energy variation will not be due to a heterogeneity of the material under inspection, but to a drop of water which has struck the jet of water which has generated it.

Accordingly, it becomes necessary to develop a suitable nozzle for applying ultrasounds, through a jet of liquid used as coupling agent to a material that will prevent drops of liquid from striking the jet itself, such that variations are avoided in the energy applied to the material under inspection. Hence, when an attenuation is detected, this will really correspond to a defect in the material under inspection.

CHARACTERIZATION OF THE INVENTION

The present invention seeks to reduce or solve one or more of the mentioned problems by means of a diffusion nozzle suitable for an ultrasound probe which utilizes water as coupling agent between a piece under inspection and an acoustic transduct such that the water is driven towards the surface of the material through a propulsion channel surrounded by a plurality of diffusion channels through which air is injected under pressure, so that the air forms an insulating screen capable of repelling the drops of water generated upon the jet of water striking the surface of the material.

One object of the present invention is an improvement in detecting heterogeneities in a material under inspection.

Another object of the present invention is to improve the reliability of the inspection process, preventing drops of liquid, generated when the jet of liquid strikes a surface of the material to be inspected, from striking the jet of liquid itself, thus preventing pieces of material without defects from being earmarked as pieces of material with defects. Accordingly, the manufacturing and inspection costs are reduced.

Another object of the present invention is to improve the reproducibility of the inspection process.

Furthermore, another object of the present invention is to reduce the time employed in aligning the ultrasound nozzles opposite one another and, therefore, the alignment of the ultrasound transducts likewise opposite one another. Hence, the time employed in the inspection process is reduced.

Another object of the present invention is to incorporate, into the automatic inspection system by ultrasounds, air barriers or curtains and, consequently, to reduce the time taken whilst carrying out inspection of each piece of material since, thanks to the air screen, at least two sets of emitter-receptor nozzles can be arranged in parallel. Accordingly, in each sweep of the nozzles a greater surface of the material under inspection can be inspected.

BRIEF EXPLANATION OF THE FIGURES

A more detailed explanation of the invention is given in the following description based on the attached figures wherein.

DESCRIPTION OF THE INVENTION

Figure 1:
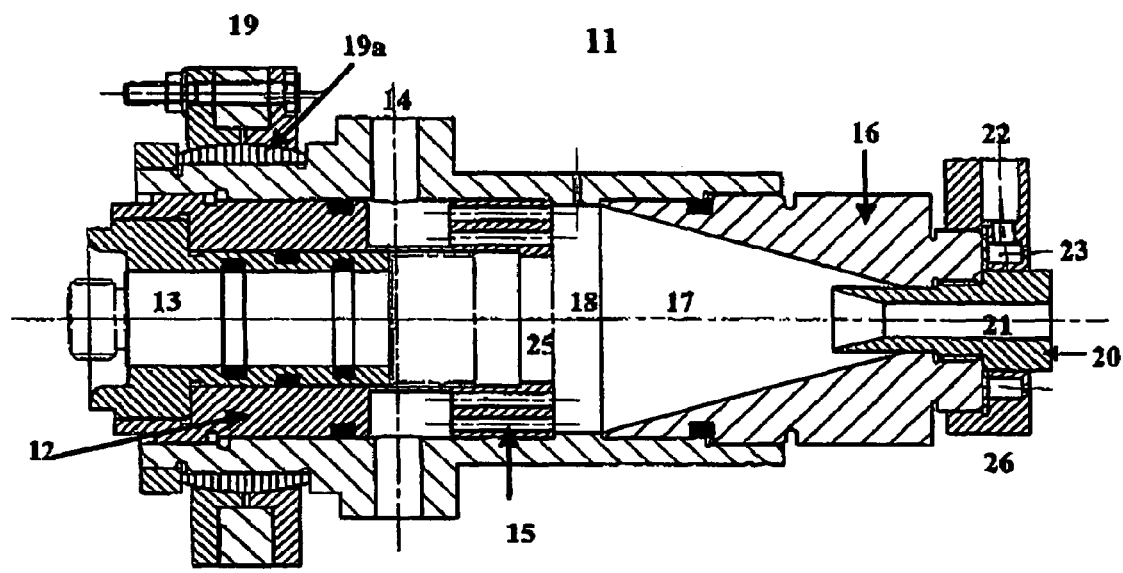
FIG. 1 is a view in cross section along a longitudinal axis of an ultrasounds probe according to the invention.

FIG. 1 shows, in cross section along a lengthwise axis, an ultrasonic probe 11 suitable for use in a system of inspection by ultrasounds, comprising a first 12 cylindrical body with revolution geometry, having inside a straight hollow cylinder 25 with circular cross section along the lengthwise axis, housing in one of its ends an ultrasonic transducer 13 which can be an emitter and/or receiver of acoustic signals, i.e., ultrasound waves.

The transduct 13 transmits the ultrasounds signal to a coupling agent, such as water, through the flat surface of one of its ends. The water is injected into the first body 12 through one or more cylindrical passages 14, open in the wall of a coupling means 19 and of the wall of the first body 12 itself, being perpendicular to the longitudinal axis, being connected with a plurality of parallel cylindrical conduits 15, along the longitudinal axis, to the straight hollow cylinder 25.

The first body 12 is connected at the end opposite to the end of the transduct 13 to a second hollow cylindrical body 16 with revolution geometry, by means of the coupling means 19, i.e., coupling support.

Coupling support 19 has mounted inside a ball joint type articulation system 19a, allowing and facilitating pointing the whole unit, i.e., alignment of the first 12 and second body 16 and, therefore, the alignment between an emitter ultrasounds probe and a receptor ultrasounds probe, each of them located at one side of the material under inspection.

The second body 16 has inside a truncuated cone type propulsion space 17 with circular cross section along the longitudinal axis, such that the base with greater diameter is nearest to the transduct 13.

It is to be observed that between the first body 12 and the second body 16 a chamber 18 is generated in which the cylindrical conduits 15 drain such that the water contacts with the flat surface of the transduct 13. As a result the first 12 and second body 16 are not in physical contact, but are coupled through the coupling support 19. These last three elements constitute the body of the probe 11.

In the smaller base of the cone 17 a diffusion nozzle 20 is coupled comprising a straight hollow cylinder 21 or propulsion channel with circular cross section along the longitudinal axis, through which the water is driven towards the surface of the material under inspection. This nozzle 20 can be interchanged with another depending on inspection needs. p Summing up, the water under pressure is injected through the cylindrical passages 14 to terminate in the chamber 18, flows along the cylindrical conduits 15 through the propulsion cone 17 and is driven towards the surface through the propulsion channel 21 of the nozzle 20.

Around propulsion channel 21 of the nozzle, a diffuser ring 26 is installed having a plurality of diffusion channels 23 with circular cross section along the longitudinal axis, distributed in its front. The diameter of the diffuser channels 23 is reduced and suitable for the passage of air at a pressure greater than atmospheric pressure.

The air under pressure is injected into the diffuser channels 23 by means of one or more openings 22 in the diffuser ring 26. Said opening 22 is perpendicular to the longitudinal axis.

The diffuser channels 23 can be distributed in accordance with different flat geometrical shapes such as a concentric circumference to propulsion channel 21 of the nozzle 20, a semi-circumference, a regular polygon or a similar shape.

According to the invention, the injected air under pressure, which passes through the opening 22 of the diffuser channels 23, forms an air insulating screen or curtain which partially or totally surrounds the jet of water driven from the nozzle 20 towards the surfaces of the material. Said barrier is capable of repelling the splashes or drops of water that are produced when the jet of water contacts or strikes the surface under inspection: hence, avoided is that said splashes strike the jet of water to provoke loss of signal, attenuations, in the inspections that are being carried out.

The air injected is capable of assuring continuity of the ultrasounds signal from the emitter transduct 13 to the receptor transduct 13 thus avoiding the possibility of interfering with the jet of water between issuing from each nozzle 20 and making contact with the surface of the piece under inspection.

The pressure at which the air is injected depends, principally, on the distance existing between the nozzle 20 and the piece of material undergoing inspection.

Figure 2:
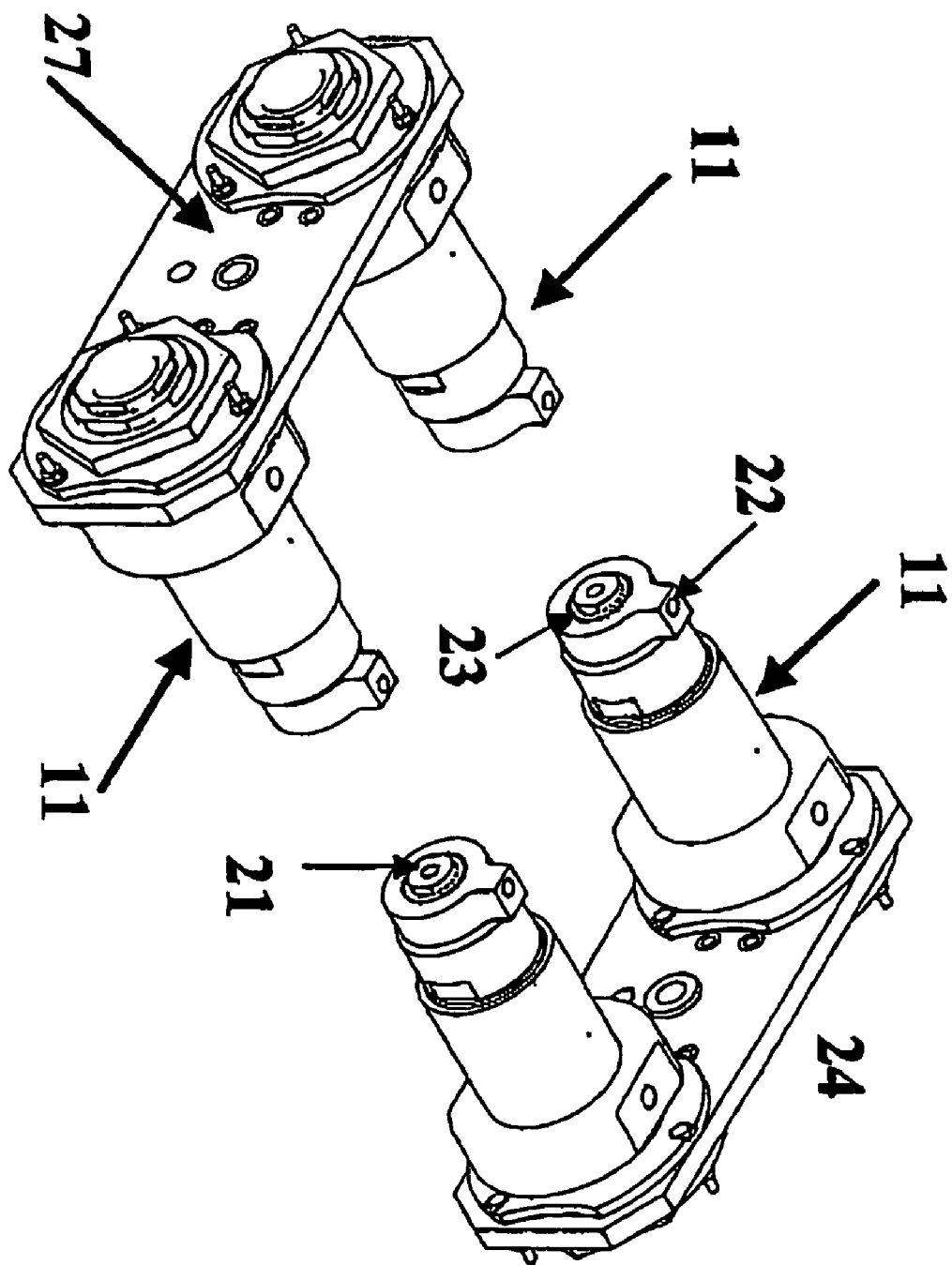
FIG. 2 is a perspective view of ultrasound probes arranged parallely according to the invention.

As seen in FIG. 2, two ultrasound probes 11 can be joined in parallel by a fastener means 24 such that between both probes an insulating barrier of air under pressure can be driven by means of the diffusion channels 23 arranged in parallel or slightly sloped with respect to the driving axis of the jet of water.

On the other hand, the two ultrasound probes 11 can be separated, besides the insulating barrier of air under pressure generated by the diffusion channels 23, by another curtain of air generated by an auxiliary diffusion means 27 attached to the holder support 24.

The invention claimed is:

1. In a diffusion nozzle (20) of an ultrasonic probe providing as coupling agent between a piece under inspection and an acoustic transducer (13) a liquid jet driven towards a surface of the piece through a propulsion channel (21), the improvements characterized in that a plurality of diffusion channels (23) surround the propulsion channel (21) for injecting gas under pressure to form a continuous insulating screen for the liquid jet.

2. Diffusion nozzle (20) according to claim 1, wherein the diffusion channels (23) are arranged parallel or slightly sloped with respect to the longitudinal axis of the propulsion channel (21).

3. Diffusion nozzle (20) according to claim 1, wherein the plurality of diffusion channels (23) are distributed in a diffusion ring (26) to form an insulating screen which envelops, totally or partially, the liquid jet.

4. Diffusion nozzle (20) according to claim 3 wherein the diffusion ring (26) includes at least one distribution channel (22) to distribute gas to the plurality of diffusion channels (23).

5. Diffusion nozzle according to claim 4 wherein the gas is air at a pressure higher than atmospheric pressure.

6. Ultrasonic probe (11) which utilizes water as coupling means between an ultrasounds transducer (13) and a material under inspection; characterised in that it comprises a first body (12) having in its interior a straight hollow cylinder (25), a second body (16) having in its interior a truncated cone type space (17), such that in its base of lesser diameter a diffusion nozzle (20) according to claim 1 is coupled, a coupling means (19) that couples the first body (12) to the second body (16), to facilitate a predetermined alignment of two ultrasound probes (11) opposite one another at both sides of the material under inspection.

7. Ultrasonic probe (11) according to claim 6 wherein the coupling means (19) include an articulation (19a) allowing to act in pivotal manner for its exact alignment with the one opposite it.

8. Ultrasonic probe (11) according to claim 7 further comprising a chamber (18) which is limited by one end of the first body (12), an end of the second body (16) and the inside walls of the coupling means (19), the first (12) and the second body (16) being housed in each of the ends of the coupling means (19), respectively.

9. Ultrasonic probe characterised in that at least two ultrasound probes (11) according to claim 6 are arranged parallel and separated at a predetermined distance from one another, by a holding means (24).

10. Ultrasonic probe according to claim 9 wherein the holding means (24) include an auxiliary diffusion means (27), between both ultrasound probes (11), for the purpose of creating an insulating air barrier between both ultrasound probes (11).

* * * * *